US008349249B2

(12) United States Patent
Wachter et al.

(10) Patent No.: US 8,349,249 B2
(45) Date of Patent: Jan. 8, 2013

(54) METAL ALLOY FOR MEDICAL DEVICES AND IMPLANTS

(75) Inventors: Jürgen Wachter, Rödermark (DE); Jens Trötzschel, Neuwiedermus (DE); Randolf Von Oepen, Aptos, CA (US)

(73) Assignees: Heraeus Precious Metals GmbH & Co. KG, Hanau (DE); Abbott Ireland, Hamilton (BM)

( * ) Notice: Subject to any disclaimer, the term of this patent is extended or adjusted under 35 U.S.C. 154(b) by 324 days.

(21) Appl. No.: 12/070,646

(22) Filed: Feb. 19, 2008

(65) Prior Publication Data

US 2008/0312740 A1 Dec. 18, 2008

Related U.S. Application Data

(63) Continuation of application No. 10/409,559, filed on Apr. 8, 2003, now abandoned.

(30) Foreign Application Priority Data

Feb. 10, 2003 (EP) .................................... 03002905

(51) Int. Cl.
*C22C 27/02* (2006.01)
*A61F 2/82* (2006.01)
(52) U.S. Cl. ........................................ 420/427; 623/1.46
(58) Field of Classification Search .................. 420/427; 623/1.49, 23.71; 148/422
See application file for complete search history.

(56) References Cited

U.S. PATENT DOCUMENTS

| | | | |
|---|---|---|---|
| 2,907,654 A | 10/1959 | Thielemann | |
| 3,128,178 A | 4/1964 | Duffek, Jr. | |
| 3,140,943 A * | 7/1964 | Field, Jr. et al. | 420/427 |
| 3,163,563 A | 12/1964 | Douglass et al. | |
| 3,173,784 A | 3/1965 | Wlodek et al. | |
| 3,183,085 A * | 5/1965 | France et al. | 420/427 |
| 3,186,837 A | 6/1965 | Duffek | |
| 3,188,206 A * | 6/1965 | Arthur | 420/426 |
| 3,249,429 A | 5/1966 | Armantrout et al. | |
| 3,254,995 A | 6/1966 | Goodfellow et al. | |
| 3,297,438 A | 1/1967 | Bradley et al. | |
| 3,317,314 A | 5/1967 | Wlodek et al. | |
| 3,341,370 A | 9/1967 | Bradley et al. | |
| 3,395,012 A | 7/1968 | McAdam et al. | |
| 3,549,429 A * | 12/1970 | Rausch et al. | 428/610 |
| 3,592,639 A | 7/1971 | Schussler et al. | |
| 3,674,572 A * | 7/1972 | Van Thyne et al. | 148/317 |
| 3,679,494 A | 7/1972 | Hill et al. | |
| 4,526,749 A | 7/1985 | Huber, Jr. et al. | |
| 4,799,977 A | 1/1989 | Rausch | |
| 4,857,269 A | 8/1989 | Wang et al. | |
| 4,859,257 A * | 8/1989 | Bates et al. | 148/422 |
| 5,049,355 A * | 9/1991 | Gennari et al. | 420/425 |
| 5,176,762 A * | 1/1993 | Berczik | 148/407 |
| 5,477,864 A * | 12/1995 | Davidson | 600/585 |
| 5,545,227 A * | 8/1996 | Davidson et al. | 623/23.53 |
| 5,630,840 A | 5/1997 | Mayer | |
| 5,690,670 A | 11/1997 | Davidson | |
| 5,728,158 A | 3/1998 | Lau et al. | |
| 5,871,595 A | 2/1999 | Ahmed et al. | |
| 5,888,201 A | 3/1999 | Stinson et al. | |
| 5,930,332 A * | 7/1999 | Eggleston et al. | 378/144 |
| 5,950,706 A * | 9/1999 | Choudhury et al. | 164/290 |
| 6,200,685 B1 * | 3/2001 | Davidson | 428/472.1 |
| 6,238,491 B1 * | 5/2001 | Davidson et al. | 148/237 |
| 6,258,182 B1 | 7/2001 | Schetky et al. | |
| 6,312,455 B2 | 11/2001 | Duerig et al. | |
| 6,368,356 B1 | 4/2002 | Zhong et al. | |
| 6,379,380 B1 | 4/2002 | Satz | |
| 6,387,121 B1 | 5/2002 | Alt | |
| 6,478,815 B1 | 11/2002 | Alt | |
| 6,707,251 B2 * | 3/2004 | Chow et al. | 313/594 |
| 6,767,418 B1 | 7/2004 | Zhang et al. | |
| 7,087,077 B1 * | 8/2006 | Van Dijk et al. | 623/1.15 |
| 7,491,234 B2 | 2/2009 | Palasis et al. | |
| 2001/0007953 A1 | 7/2001 | Duerig et al. | |
| 2002/0008021 A1 | 1/2002 | Weigert et al. | 204/298.12 |
| 2002/0095207 A1 | 7/2002 | Moriuchi et al. | |
| 2002/0111694 A1 | 8/2002 | Ellingsen et al. | |
| 2002/0139667 A1 * | 10/2002 | Wang | 204/298.13 |
| 2003/0037847 A1 * | 2/2003 | Michaluk et al. | 148/422 |
| 2003/0106888 A1 * | 6/2003 | Gnesin et al. | 219/553 |
| 2003/0125808 A1 * | 7/2003 | Hunter et al. | 623/18.11 |
| 2003/0186914 A1 | 10/2003 | Hofer et al. | |
| 2004/0062676 A1 | 4/2004 | Trotzschal et al. | |
| 2004/0126613 A1 * | 7/2004 | Bewlay et al. | 428/663 |

(Continued)

FOREIGN PATENT DOCUMENTS

DE 1 123 836 2/1962

(Continued)

OTHER PUBLICATIONS

Office Action issued May 6, 2010 in U.S. Appl. No. 11/804,044.
Office Action issued Nov. 20, 2009 for U.S. Appl. No. 11/804,044.
Advisory Action dated Oct. 22, 2009 in U.S. Appl. No. 11/804,044.
Office Action issued Jun. 8, 2009 for U.S. Appl. No. 11/804,044.
Amon et al: Introduction of a New Coronary Stent with Enhanced Radioopacity and Hemocompatibility, 1999 III-EMBC and CMBEC; pp. 107-108.
Office Action issued Aug. 21, 2008 for U.S. Appl. No. 11/804,044.
Office Action issued Nov. 8, 2010 in U.S. Appl. No. 11/804,029.

(Continued)

*Primary Examiner* — Christopher Koharski
*Assistant Examiner* — Cheryl Miller
(74) *Attorney, Agent, or Firm* — Panitch Schwarze Belisario & Nadel LLP

(57) ABSTRACT

The present invention relates to a medical device or implant made at least in part of a high strength, low modulus metal alloy comprising Niobium, Tantalum, and at least one element selected from the group consisting of Zirconium, Tungsten and Molybdenum. The medical devices according to the present invention provide superior characteristics with regard to biocompatibility, radio-opacity and MRI compatibility.

4 Claims, No Drawings

U.S. PATENT DOCUMENTS

| | | | |
|---|---|---|---|
| 2004/0158309 | A1 | 8/2004 | Wachter et al. |
| 2004/0168751 | A1* | 9/2004 | Wu .............................. 148/421 |
| 2004/0243133 | A1* | 12/2004 | Materna .......................... 606/76 |
| 2004/0249447 | A1* | 12/2004 | Boylan et al. ................. 623/1.19 |
| 2007/0221300 | A1 | 9/2007 | Wachter et al. |
| 2007/0276488 | A1 | 11/2007 | Wachter et al. |
| 2008/0038146 | A1 | 2/2008 | Wachter et al. |
| 2010/0222866 | A1 | 9/2010 | Wachter et al. |

FOREIGN PATENT DOCUMENTS

| | | |
|---|---|---|
| DE | 1 258 108 | 1/1968 |
| DE | 42 43 757 | 6/1994 |
| DE | 29806959 U1 | 9/1999 |
| EP | 0 092 477 | 10/1983 |
| EP | 359 446 | 3/1990 |
| EP | 437 079 | 7/1991 |
| EP | 601 804 | 6/1994 |
| EP | 707 085 | 4/1996 |
| EP | 788 802 | 8/1997 |
| EP | 1 046 722 | 10/2000 |
| EP | 1 186 682 | 3/2002 |
| EP | 1 403 390 | 3/2004 |
| EP | 1444993 A1 | 8/2004 |
| FR | 2 566 804 | 1/1986 |
| GB | 933 712 | 8/1963 |
| GB | 933712 * | 8/1963 |
| JP | 61-124566 | 6/1986 |
| JP | 04-184732 | 7/1992 |
| JP | 08-041611 A | 2/1996 |
| JP | 08-299428 A | 11/1996 |
| JP | 2001-003127 A | 1/2001 |
| WO | WO 99/58184 | 11/1999 |
| WO | WO 00/68448 | 11/2000 |
| WO | WO 02/05863 | 1/2002 |
| WO | 0220873 A2 | 3/2002 |
| WO | WO 02/38080 | 5/2002 |
| WO | WO 02/43787 | 6/2002 |
| WO | 2006076447 A2 | 7/2006 |

OTHER PUBLICATIONS

ASM International, Materials Park, Ohio, Properties and Selection: Nonferrous Alloys and Special-Purpose Materials: "Preparation and Characterization of Pure Metals", Oct. 1990, vol. 2, pp. 1093-1097.
Office Action issued Apr. 6, 2010 for U.S. Appl. No. 11/804,029.
Office Action issued Sep. 8, 2009 in U.S. Appl. No. 11/804,029.
Office Action issued Dec. 23, 2008 for U.S. Appl. No. 11/804,029.
Office Action issued Jan. 7, 2009 in U.S. Appl. No. 11/804,040.
Office Action issued Sep. 18, 2009 in U.S. Appl. No. 11/804,040.
Office Action issued Feb. 3, 2010 in U.S. Appl. No. 11/804,040.
Office Action issued Aug. 11, 2010 in U.S. Appl. No. 11/804,040.
Office Action issued Jul. 5, 2005 in US Appl. No. 10/409,559.
Office Action issued Jan. 19, 2006 in U.S. Appl. No. 10/409,559.
Office Action issued Aug. 23, 2006 in U.S. Appl. No. 10/409,559.
Office Action issued Apr. 13, 2007 in U.S. Appl. No. 10/409,559.
Office Action issued Mar. 17, 2011 in U.S. Appl. No. 11/804,044.
Cabot Supermetals Product Information. ASTM Standards: Chemical Requirements for Tantalum. www.cabot-corp.com—available on Mar. 10, 2010.
ASTM: Designation B 365-98, Standard Specification for Tantalum and Tantalum Alloy Rod and Wire. ASTM International.
Declaration by Professor Alfons Fischer, University Duisburg-Essen, Material Sciences Chair, dated Feb. 28, 2010.
O'Brien et al., Biomaterials 29 (2008) 4540-4545.
O'Brien et al., Journal of the Mechanical Behavior of Biomedical Materials 1 (2008) 303-312.
Test report filed in examination proceedings on Jul. 13, 2005.
U.S. Office Action issued on Apr. 26, 2012 in U.S. Appl. No. 11/804,029.
U.S. Appl. No. 13/480,922 by Wachter, filed May 25, 2012.
U.S. Appl. No. 13/481,017 by Wachter, filed May 25, 2012.
U.S. Appl. No. 11/460,697, filed Jul. 28, 2006.

* cited by examiner

METAL ALLOY FOR MEDICAL DEVICES AND IMPLANTS

This is a Continuation under 35 U.S.C. 1.53(b) of U.S. patent application Ser. No. 10/409,559 filed Apr. 8, 2003 now abandoned. The entire contents of U.S. application Ser. No. 10/409,559 are incorporated herein by reference. Priority is claimed on that application and on the following application:

Country: European Application No. 03002905.2, filed Feb. 10, 2003

The present invention relates to an improved metal alloy for medical implants or devices for desired material properties.

BACKGROUND OF THE INVENTION

A medical implant or device must satisfy a number of requirements. Factors affecting the choice of the medical implant or device and the material thereof are mainly all mechanical properties and biocompatibility. The material must not cause any inflammatory reaction or allergic reaction. Commonly used materials often include nickel, like medical grade 316L stainless steel, which contains about 16% nickel. For patients with an allergic reaction the implantation of such materials is contraindicated. Another consideration in material selection is the need for the implanting physician to be able to visualize the position of the medical implant or device during procedure to the desired target site in the body, and for purposes of examination from time to time thereafter at the implant site, typically by X-ray fluoroscopy.

With the growing importance of magnetic resonance imaging (MRI), MRI compatibility is desirable. The metal alloys commonly used for implantation (like stainless steel 316) induce a local disturbance of the magnetic field used in MRI, to the extent that imaging of surrounding tissue is impeded. Although alloys like Nitinol behave more favourably in MRI, their MRI compatibility is not considered to be sufficiently good.

This invention relates to medical devices or implants in general such as catheters, guide wires, stents, stent grafts and heart valve repair devices.

Stents are generally thin walled tubular-shaped devices composed of complex patterns of inter-connecting struts which function to hold open a segment of a blood vessel or other body lumen like oesophagus and urethra. Stent grafts are stents with a circumferential covering or lining and are suitable for supporting a dissected artery or intimal flap that can occlude a vessel lumen. Stents and stent grafts are typically implanted by use of a catheter. Initially they are maintained in a radially compressed state to manoeuvre them through the lumen. Once in position, they are deployed. The material from which the vascular prosthesis like stents or stent grafts is constructed must allow the prosthesis to undergo expansion, which typically requires substantial deformation. Once expanded the stent must maintain its size and shape and must be capable of withstanding the structural loads, namely radial compressive forces, imposed on the stent as it supports the walls of a vessel lumen. The wall of the prosthesis must be sufficiently thick, depending on the stent material, not only to withstand the vessel wall recoil but also allow the stent to be seen on the fluoroscope. Finally, the prosthesis material must be biocompatible so as not to trigger any adverse vascular responses like restenosis or thrombus formation in the treated vessel.

For medical devices such as all kind of catheters and guide wires special mechanical properties are desired to have perfect trackability and pushability during the intervention. Moreover, good radio-opacity and MRI compatibility are essential in order to survey medical procedures via x-ray and MRI. Finally also for these medical devices biocompatibility is a must.

In the past years increased effort was undertaken to find new materials for medical implants and devices bearing superior characteristics over commonly used metals like stainless steel or titanium. Numerous publications focus on titanium alloys aiming at corrosion resistant, high strength and biocompatible alloys. As described for example in U.S. Pat. No. 6,312,455, US 2001/0007953, and WO 99/58184 many Titanium-alloys thereof are super-elastic or shape memory alloys. A pseudo-elastic β-titanium alloy fabricated from Titanium, Molybdenum, Aluminium and optionally Niobium, Chrome and Vanadium is described in U.S. Pat. No. 6,258,182. EP 0 788 802 provides a self-expanding stent consisting of a titanium alloy including at least about 68 weight percent titanium and optionally Niobium, Zirconium, and Molybdenum. U.S. Pat. No. 6,238,491 and WO 00/68448 describe a Niobium-Titanium-Zirconium-Molybdenum alloy for medical devices providing a uniform β-structure, which is corrosion resistant, and can be processed to develop high-strength and low-modulus. The alloy comprises 29 to 70 weight percent Niobium, 10 to 46 weight percent Zirconium, 3 to 15 weight percent Molybdenum and a balance of Titanium. In another approach Davidson (EP 0 601 804) employ an alloy consisting essentially of Titanium, 10 to 20 or 25 to 50 weight percent Niobium and optionally up to 20 weight percent Zirconium, the alloy having an elastic modulus less than 90 GPa. Similar Titanium-alloys for medical implants also published by Davidson comprise Titanium, 10 to 20 or 35 to 50 weight percent Niobium and optionally up to 20 weight percent each Zirconium and Tantalum (EP 0 437 079) or Titanium, 10 to 20 or 35 to 50 weight percent each Niobium and Tantalum and optionally up to 20 weight percent Zirconium (U.S. Pat. No. 5,690,670). EP 0 707 085 also provides a low modulus, biocompatible Titanium-base alloy for medical devices consisting of 20 to 40 weight percent Niobium, 4.5 to 25 weight percent Tantalum, 2.5 to 13 weight percent Zirconium and the balance Titanium. A further high strength, low modulus and biocompatible Titanium-alloy is laid open in U.S. Pat. No. 4,857,269 and EP 0 359 446 consisting of Titanium and up to 25 weight percent Niobium, Zirconium, and Molybdenum. EP 1 046 722 describes a corrosion resistant Titanium-Zirconium-type alloy for medical appliances consisting of 25 to 50 weight percent Titanium, 5 to 30 weight percent Niobium, 5 to 40 weight percent Tantalum and 25 to 60 weight percent Zirconium.

Further approaches to develop biocompatible, high strength alloys which are also sufficiently radio-opaque and do not contain Titanium are described in U.S. Pat. No. 6,478,815 and WO 02/43787. Both documents reveal stents made from at least 90 weight percent Niobium. Niobium is a relatively soft and ductile metal, which is alloyed with traces of other elements, e.g. Zirconium, Tantalum or Titanium for reinforcement of the alloy. However, Niobium surfaces cannot be electropolished because of their tendency to smear. Stents fabricated from binary Tantalum-Alloys, namely Tantalum-Niobium and Tantalum-Tungsten, are disclosed in WO 02/05863.

DETAILED DESCRIPTION OF THE INVENTION

Aim of the present invention is to provide an inventive material for medical implants and devices, which comprises favourable mechanical properties, excellent biocompatibility, optimal radio-opacity while at the same time exhibiting minor image artefact in MRI examination (MRI compatibility) and does therefore overcome the drawbacks of recently available metals for medical purposes.

The alloy fulfills all mechanical and structural requirements according to its function in a medical implant or device. Moreover, the device is sufficiently radio-opaque to allow for good imaging of the device under x-ray without the addition of an extra layer or portion of radio-opaque material. Also, the device is not overly bright and therefore does not obscure the image of the surrounding tissue, as would be the case with a device made from an extremely dense material. In addition, the device is MRI safe and compatible, preferably also visible under MRI.

Surprisingly, it has been found that the desired properties can be given to a metal alloy comprising Tantalum, Niobium and at least one element selected from the group consisting of Tungsten, Zirconium and Molybdenum.

Tantalum is known as a very hard metal with a high melting point, high strength, and good ductility and is almost completely inert at body temperature. Tantalum has a high atomic number (73) and a density of 16.6 g/cm$^3$ resulting in a high radio-opacity. Therefore, medical implants or devices made of pure tantalum have the disadvantage that they are excessively radio-opaque, leading to a completely black area on the x-ray image in the region where the medical implant or device is located.

The radio-opacity of the inventive metal alloy is adjusted by adding further elements possessing higher or lower atomic numbers to the tantalum based alloy, which lowers the density of the alloy. Niobium has an atomic mass of approximately half that of Tantalum. Thus, tailoring the density of the inventive alloy by variation of the Niobium portion allows achievement of appropriate radio-opacity for each medical device or implant manufactured at least in part of the inventive alloy. It is possible to fabricate an alloy according to the present invention, which is sufficiently radio-opaque to be readily visualized under x-ray during medical procedures and yet is not so radio-opaque as to interfere with the visualization of surrounding body tissue.

The alloys of the invention show excellent melting and mixing properties with excellent uniformity since Niobium and tantalum are arbitrarily miscible. Varying the amount of Tungsten, Zirconium and Molybdenum, or optionally, the amount of Cerium, Rhenium, or Hafnium, allows adjustment of the granular size of the alloy.

Surprisingly, the alloy according to the present invention is stronger than pure tantalum and in specific compositions even stronger than stainless steel. In a preferred embodiment a stent is manufactured from the alloy of the invention comprising a tailored radio-opacity while having a reduced wall thickness. Such a stent combines desired visibility under x-ray and excellent radial force with minimized delivery profile and less turbulence when employed in the vessel.

An additional advantage of the inventive alloy is the formation of a passive oxide film primarily composed of Tantalum-oxide ($Ta_2O_5$), which is generally more durable and more corrosion resistant than for example the chromium-oxide film formed during the passivation of stainless steel.

The inventive alloy can be easily cold-worked to increase strength and reduce elastic modulus. It is possible to form a hard, abrasion resistant surface on the inventive alloy through standard oxidation and nitridizing methods known by those skilled in the art. The presence of a hard, inert, abrasion resistant surface layer presents an important option for medical implants and devices in which it is desirable to have lower friction and wear, electrical insulation and improved corrosion resistance.

To further improve the biocompatibility of the medical implant or device fabricated at least in part from the inventive alloy, at least a portion of the surface of the inventive alloy can be conversion surface hardened and/or coated. Such coatings can include, but are not limited to a polymer, a blend of polymers, a metal, a blend of metals, a ceramic and/or biomolecules, in particular peptides, proteins, lipids, carbohydrates and/or nucleic acids (e.g. collagen, heparin, fibrin, phosphorylcholine, cellulose, morphogenic proteins or peptides, growth factors). Furthermore the alloy surface or the coatings can comprise stem cells and/or a bioactive substances, in particular drugs, antibiotics, growth factors, anti-inflammatory agents and/or anti-thrombogenic agents. Further, the surface can be modified by electropolishing or mechanical polishing for formation of a completely smooth surface, sintering to achieve a porous coating as for example described in EP0601804, or by roughening procedures or microblasting, in particular sandblasting, to achieve a rough surface.

The inventive alloy is useful in the manufacturing of a variety of medical implants and devices. The manufacture of medical devices from the invention alloy includes minimal-invasive devices, in particular guide wires, catheters (balloon catheters, guiding catheter, angiographic catheters, functional catheters, . . . ), intra-cavernous implants, in particular intra-oesophagus, intra-urethra, intra-tracheal implants and intra-vascular implants, in particular stents, stent grafts, stent graft connector, heart valve repair device or filters.

Preferred alloys contain the following elements:
(a) between about 0.1 and 70 weight percent Niobium,
(b) between about 0.1 and 30 weight percent in total of at least one element selected from the group consisting of Tungsten, Zirconium and Molybdenum,
(c) up to 5 weight percent in total of at least one element selected from the group consisting of Hafnium, Rhenium and Lanthanides, in particular Cerium,
(d) and a balance of Tantalum The alloys preferably provide for a uniform beta structure, which is uniform and corrosion resistant, and have the ability for conversion oxidation or nitridization surface hardening of the medical implant or device.

The tungsten content is preferably between 0.1 and 15 weight percent.

The zirconium content is preferably between 0.1 and 10 weight percent.

The molybdenum content is preferably between 0.1 and 20 weight percent and more preferably between 0.1 and 10 weight percent.

The niobium content is preferably between 5 and 25 weight percent.

Especially preferred alloys contain about 10 weight percent Niobium and about 2.5 weight percent Tungsten.

Also preferred are alloys which comprise about 10 weight percent Niobium and about 7.5 weight percent Tungsten.

Also preferred are alloys which comprise about 10 weight percent Niobium and about 1 weight percent Zirconium.

Also preferred are alloys which comprise about 10 weight percent Niobium and about 3 weight percent Zirconium.

The invention also relates to medical implants or devices fabricated from the above-mentioned alloys, e.g. minimal-invasive devices, in particular catheters or guide wires, or intra-cavernous implants, in particular intravascular implants, such as stents, a stent grafts, stent graft connectors or heart valve repair devices.

In the above implants and devices the surface of the metal alloys may be passivated by oxidation or nitridization, or may be electropolished, mechanically polished, micro blasted, roughened or sintered, or may be coated with a polymer, a blend of polymers, a metal, a blend of metals, a ceramic and/or biomolecules, in particular peptides, proteins, lipids, carbohydrates and/or nucleic acids; or may be coated with stem cells and/or a bioactive substance, in particular drugs, antibiotics, growth factors, anti-inflammatory agents and/or anti-thrombogenic agents.

EXAMPLE

The invention may be carried out with an alloy of the following composition:
Ta: 71.5
Nb: 27.5
Zr: 1.0

Methods of producing the alloy are known to the person skilled in the art.

The invention claimed is:

1. A medical implant or medical device comprising components at least partially fabricated from a tantalum-based metal alloy, wherein the tantalum-based metal alloy consists essentially of:
   (a) about 10 weight percent niobium;
   (b) about 1 weight percent of zirconium;
   (c) up to 5 weight percent in total of at least one element selected from the group consisting of hafnium, rhenium and lanthanides;
   (d) and a balance of tantalum, and
   wherein the tantalum-based metal alloy has a surface coated with at least one of the group consisting of a polymer, a blend of polymers, and biomolecules.

2. A medical implant or medical device according to claim 1, wherein the surface of the tantalum-based metal alloy is coated by at least one of the group consisting of peptides, proteins, lipids, carbohydrates and nucleic acids.

3. A medical implant or medical device comprising components at least partially fabricated from a tantalum-based metal alloy, wherein the tantalum-based metal alloy consists essentially of:
   (a) about 10 weight percent niobium;
   (b) about 1 weight percent of zirconium;
   (c) up to 5 weight percent in total of at least one element selected from the group consisting of hafnium, rhenium and lanthanides;
   (d) and a balance of tantalum, and
   wherein the tantalum-based metal alloy has a surface coated with at least one of stem cells and a bioactive substance.

4. A medical implant or medical device according to claim 3, wherein the surface of the tantalum-based metal alloy is coated with at least one of the group consisting of drugs, antibiotics, growth factors, anti-inflammatory agents, and anti-thrombogenic agents.

* * * * *